United States Patent [19]

Pointier

[11] Patent Number: 4,780,370

[45] Date of Patent: Oct. 25, 1988

[54] POWDER COMPOSITION FOR ASHTRAY USE AND METHOD FOR ITS MANUFACTURE

[76] Inventor: Alain J. Pointier, 82 Rue Diderot, 92500 Rueil Malmaison, France

[21] Appl. No.: 61,773

[22] Filed: Jun. 15, 1987

[30] Foreign Application Priority Data

Jun. 16, 1986 [FR] France ............................ 86 08662

[51] Int. Cl.⁴ .......................... B05D 1/36; B05D 7/00
[52] U.S. Cl. .................................. 428/404; 428/331; 428/357; 428/402; 428/403; 428/905
[58] Field of Search .............. 428/357, 331, 905, 403, 428/405, 402, 404

[56] References Cited

FOREIGN PATENT DOCUMENTS 70373 6/1979 Japan .................................. 428/905

*Primary Examiner*—Sharon A. Gibson
*Attorney, Agent, or Firm*—Larson and Taylor

[57] ABSTRACT

Powdered composition for ashtray use, comprising a powdered mass constituted by silica, impregnated by at least one odor-absorbing product adapted to absorb the odors of tobacco ash, fag-ends, or cigar butts, etc. This odor-absorbing product can advantageously be ricinoleate or grillocin; preferably, the impregnation products comprise the odor-absorbing product (5 to 15%), perfume (35 to 45%) and a solvent (50%).

5 Claims, No Drawings

POWDER COMPOSITION FOR ASHTRAY USE AND METHOD FOR ITS MANUFACTURE

The present invention relates to a powder composition for ashtray use, comprising a powdered mass constituted by silica, and it also relates to a method for its manufacture.

Various powder compositions are already known intended for avoiding the diffusion of undesirable odors, particularly odors released by tobacco ash, fag-ends or cigar butts, etc. These known compositions generally have the common feature of including a granular mass constituted at least to a large extent by silica, which is impregnated by a perfumed additive.

The essential drawback of these known compositions is that the function of absorbing undesirable odors is left to the granular mass alone although this granular mass certainly possesses good extinguishing properties for smothering incandescent portions, however it has only mediocre effectiveness for absorbing odors. These prior art products have hence essentially the capacity of enabling the odorous release of the perfumed additive which becomes added to the undesirable odor, to mask the latter as far as possible. The result thereof is a highly charged atmosphere and the mixture of smells which arises therefrom may prove to be scarcely pleasant and poorly tolerated.

In addition, the perfumed additive which is added to the granular mass, in a product available in the trade, retains its fatty residues which causes agglomeration of the grains and reduces the flow properties of the granular mass; in addition, this product makes greasy the objects with which it is placed in contact, which thereby considerably limits the conditions of use.

It is an essential object of the invention to provide a powder composition for ashtray use which does not show the drawbacks of the products known at present and which responds better to the various exigencies of practice.

For this purpose, according to a first aspect of the invention there is provided a powder composition for ashtray use, comprising a powder mass constituted by silica, which is characterized in that this powder mass is impregnated by at least one odor-absorbing product adapted to absorb the smells of tobacco, tobacco ash, tars, etc., released by tobacco ash, and/or fag-ends, cigar butts, etc., and the odor-absorbant product can advantageously be ricinoleate or grillocin.

Through this fact, the composition according to the invention is suitable for ensuring effective and efficient deodorization by absorbing the odors released by tobacco ash, fag-ends or cigar butts, etc., whilst preserving its useful extinguishing property.

It is still possible to impregnate the powder mass with other additives, in particular with a perfume; but in this case the perfume is no longer for the purpose of combatting undesirable emanations: it may be freely selected and especially it may be dosed to provide as discreet a release as desired.

Advantageously in this case, the impregnation products are present in the following proportions by weight:

| | |
|---|---|
| odor-absorbing product | 5 to 15% |
| perfume (35–45% extract) | 35 to 45% |
| solvent | 50% |

The solvent (for example that marketed under the name Shell T) ensures the removal of the fatty residues from the perfume and permits a completely dry powdered mass to be obtained, which is non-sticky, non-greasy, and free-flowing.

Of couse, it is possible to provide for the powdered mass to be colored.

A second aspect of the invention is directed to a method for the preparation of a powdered composition for ashtray use, comprising a powdered mass constituted by silica, which is characterized by the following steps:

heating and mixing the powdered mass.

then spraying, onto this heated and mixed powdered mass, a liquid solution containing at least one odor-absorbant product, particularly ricinoleate or grillocin.

Preferably, the heating of the powdered mass is effectuated at a temperature comprised between about 180° and 220° C., preferably about 200° C.

As the case may warrant, before carrying out the spraying of the liquid solution, the powdered mass is dyed by soaking and stirring in a liquid dye bath containing pasty hydroplasts diluted in a dispersion liquid, then by heating to a temperature comprised between about 180° and 220° C. the evaporation of the liquid phase, the aforesaid spraying of the liquid solution being done at the end of the drying step.

By means of the method according to the invention, there is obtained a powder composition which is completely dry and which therefore preserves fully its free-flowing character. This composition possesses an excellent power of absorption of odors of tobacco ash and fag-ends, can release a discrete perfume, is aesthetically pleasant, and does not stain the articles with which it is in contact. Its action is permanent, and not momentaneous like the various aerosols or candles at present used for this same purpose. In addition, its cost of manufacture remains modest and it can be obtained in large amounts and automatically by simple industrial production processes.

Simple in use, this powder composition is designed for individual, collective or special ashtrays, such as those used in hotels or aircraft, by procuring added security against fires by reason of its high extinguishing power.

It is desirable to select a silica of fairly fine particle size comprised between 200 and 400 μm, preferably of the order of 300 μm, that is to say a silica of glass-making quality having a selected constant and permanent granulometry.

The adjuvants sprayed onto the silica are present in the proportion of 5 to 15% for the odor-absorbing product, 35 to 45% for the perfume and about 50% for the solvent (proportions by weight).

The amount of perfume incorporated may be 4 grams per liter of silica, with 35–40% extract, with various adjuvants such as a fixing agent. By way of example, it is possible to use the following perfume compositions:

EXAMPLE 1 (green-colored composition):

| | |
|---|---|
| Citral | 2% |

-continued

| Libsea Cubeba | 5% |
|---|---|
| Mint Terpenes | 2% |
| Citrus composition | 71% |
| Fixing agent | 20% |

EXAMPLE 2 (yellow-colored composition):

| Jasmin base | 5% |
|---|---|
| Opopanax base | 5% |
| Spiced base | 10% |
| Carnation base | 2% |
| Arora CX | 8% |
| Floral composition | 50% |
| Fixing agent | 20% |

EXAMPLE 3 (blue-colored composition):

| Lavender 50-52 | 10% |
|---|---|
| Fine lavender | 3.5% |
| Fine absolute lavender | 10% |
| Coumarin | 1% |
| Lavender fixing agent | 5.7% |
| Benzyl benzoate | 25% |
| Reinforcing agent | 2.9% |
| Amber musk | 5.7% |
| Fixing agent | 5.7% |

-continued

| Base composition | 30.5% |
|---|---|

As is self-evident and as emerges already besides from the foregoing, the invention is in no way limited to its methods of application and embodiments which have been more especially envisaged; it encompasses thereof, on the contrary, all modifications.

I claim:

1. Powder composition for ashtray use, comprising a power mass of silica, impregnated with at least one odor-absorbing product selected from the group consisting of ricinoleate and grillocin.

2. Composition according to claim 1, wherein the powder mass is impregnated in addition with a product containing at least one perfume and at least one solvent.

3. Composition according to claim 2, wherein the impregnation products are present in the following proportions by weight:

| odor-absorbing product | 5 to 15% |
|---|---|
| perfume (35-45% extract) | 35 to 45% |
| solvent | 50% |

4. Composition according to claim 1, wherein the powder mass is colored.

5. Composition according to claim 1 wherein the granulometry of the powder mass is approximately uniform and comprised between 200 and 400 μm.

* * * * *